US010011876B2

(12) United States Patent
Kandula

(10) Patent No.: US 10,011,876 B2
(45) Date of Patent: Jul. 3, 2018

(54) METHOD AND SYSTEM FOR PROGNOSIS AND TREATMENT OF DISEASES USING PORTFOLIO OF GENES

(75) Inventor: Mahesh Kandula, Andhra Pradesh (IN)

(73) Assignee: KRISANI BIOSCIENCES PVT. LTD, Hyerabad, AP (IN)

(*) Notice: Subject to any disclaimer, the term of this patent is extended or adjusted under 35 U.S.C. 154(b) by 940 days.

(21) Appl. No.: 13/988,764

(22) PCT Filed: Jun. 21, 2011

(86) PCT No.: PCT/IN2011/000417
§ 371 (c)(1),
(2), (4) Date: May 22, 2013

(87) PCT Pub. No.: WO2012/070056
PCT Pub. Date: May 31, 2012

(65) Prior Publication Data
US 2013/0244901 A1    Sep. 19, 2013

Related U.S. Application Data

(60) Provisional application No. 61/429,857, filed on Jan. 5, 2011.

(30) Foreign Application Priority Data

Nov. 23, 2010 (IN) .......................... 3524/CHE/2010

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
CPC ............ C12Q 1/6886; C12Q 2600/106; C12Q 2600/158
See application file for complete search history.

(56) References Cited

U.S. PATENT DOCUMENTS 6,263,287 B1 * 7/2001 Zheng ................... G06F 19/20
435/4
7,473,526 B2    1/2009 Wang
(Continued)

FOREIGN PATENT DOCUMENTS

WO        2001016858 A2    3/2001

OTHER PUBLICATIONS

Tricarico et al., Quantitative real-time reverse transcription polymerase chain reaction: normalization to rRNA or single housekeeping genes is inappropriate for human tissue biopsies.*
(Continued)

*Primary Examiner* — Reza Ghafoorian
(74) *Attorney, Agent, or Firm* — Raj Abhyanker, P.C.

(57) ABSTRACT

This disclosure generally relates to a method, a system and a kit for diagnosing and treating various disease conditions using the gene expression value in a given sample obtained from a subject. This disclosure further relates to selecting the right set of genes as a portfolio of genes for a particular disease. Providing a set of appropriate portfolio of gene for studying the gene expression values and using the values as a diagnostic tool is also disclosed. The gene expression value is further used for intervention by pharmaceuticals as a prediction model for the treatment of the disease. An individual may have a personalized health card that may store the gene expression value for that particular individual. A system may store the data for portability and integrated view of the individual's medical data for effective diagnosis and treatment.

7 Claims, 4 Drawing Sheets

(56) References Cited

U.S. PATENT DOCUMENTS

| | | | |
|---|---|---|---|
| 7,569,345 B2 | 8/2009 | Cobleigh et al. | |
| 7,640,114 B2 | 12/2009 | Showe et al. | |
| 8,055,452 B2 | 11/2011 | Bevilacqua et al. | |
| 2003/0224374 A1* | 12/2003 | Dai | C12Q 1/6886 |
| | | | 435/6.14 |
| 2004/0110201 A1 | 6/2004 | Ayoub Rashtchian et al. | |
| 2005/0227221 A1* | 10/2005 | Minor | G01N 33/5005 |
| | | | 435/4 |
| 2009/0298052 A1 | 12/2009 | Atkins et al. | |

OTHER PUBLICATIONS

Hamalainen et al., Identification and Validation of Endogenous Reference Genes for Expression Profiling of T Helper Cell Differentiation by Quantitative Real-Time RT-PCR.*

* cited by examiner

METHOD AND TREATMENT USING GENE EXPRESSION PORTFOLIO 100

METHOD AND SYSTEM FOR PROGNOSIS AND TREATMENT OF DISEASES USING PORTFOLIO OF GENES

CROSS REFERENCE TO RELATED APPLICATION

This disclosure claims priority to PCT application serial no. PCT/IN2011/000417 filed on Jun. 21, 2011, which, in turn, claims priority to U.S. Provisional application 61/429, 857 filed on Jan. 5, 2011 and Indian Provisional application 3524/CHE/2010 filed on Nov. 23, 2010. These disclosures are hereby incorporated by this reference in their entireties for all of their teachings.

SEQUENCE LISTING

The instant application contains a Sequence Listing which has been submitted in ASCII format via EFS-Web and is hereby incorporated by reference in its entirety. Said ASCII copy, is named 00071 00008 US1 SEQ ST25 and is 10 kB in size.

FIELD OF TECHNOLOGY

This disclosure generally relates to a method, a system and a kit for diagnosing and treating various disease conditions using the gene portfolio in a subject. More specifically, the portfolio of gene and their expression value may be used for tool by the treatment provider as a prognostic model and change in treatment regimen for a particular disease.

BACKGROUND

In women, two of the most widely used screening tests are the Papanicolaou (PAP) test to detect cervical cancer and mammography to detect breast cancer. Both screening tests have been successful in reducing the death rates from these cancer in certain age groups. There are still many cases that are not detected through these techniques and the mortality rate is very high due to high cost, lack of insurance coverage and reluctance.

In the case of breast cancer, great efforts have been made to develop a detection test by mammography. Although several studies indicate that mass mammography may be a useful strategy to reduce breast cancer mortality, this method involves a certain number of disadvantages. Some of the disadvantages are a high rate of false positives, frequent false negatives and enormous public health costs. Thus, when the benefits are weighed against these advantages, it is not surprising that this form of screening has engendered contentious debates over the last twenty 30 years.

In men, prostate-specific antigen (PSA) levels in the blood may be used to screen for prostate cancer. PSA levels are high in men with prostate cancer, but levels also are elevated in men with noncancerous (benign) enlargement of the prostate. Currently the main drawback to its use as a screening test is the large number of false-positive results, which generally lead to more invasive tests.

It is known that diagnosis and follow up of the evolution of cancer are carried out, besides direct observation of the tumors, by biopsy analysis or in the case of blood malignancies by analysis of the bone marrow, which implies either a surgical intervention, or an invasive test such as a biopsy or a bone marrow aspiration. Now, in addition to the disagreeable or even dangerous aspect of such methods, it has been observed that they may not be very precise. Current methods for classifying human malignancies are mostly to rely on a variety of morphological, clinical and molecular variables. Despite recent progress, there are still many uncertainties in diagnosis. Furthermore, it is likely that the existing classes of the tumors are heterogeneous and comprise diseases that are molecularly distant.

SUMMARY

In this disclosure a method, system and kit are being presented which may be used for diagnosis, prognosis and/or for monitoring the treatment regimen. In one embodiment, a method of diagnosing a disease using a portfolio of genes that is specific for an individual or for the disease or for a subject is being disclosed. In another embodiment, gene expression values are measured and used for evaluating the presence and/or absence of the disease condition in a subject.

In another embodiment, a method of developing a gene expression values for the portfolio of genes that are specific to the profile indicative of the presence or stage of a selected disease, disorder or genetic pathology is being presented.

In one embodiment, a mathematical algorithm is executed on a computer readable medium to select a portfolio of genes to diagnose a particular disease using the metabolic pathway.

In another embodiment, a predictive mathematical expression value is displayed to show the portfolio of genes affected for a specific disease. In another embodiment, suggestive inhibitors and enhancers for a particular gene expression value are proposed as a pharmaceutical treatment option. In another embodiment, a treatment provider may input the existing treatment regime and observe the effect of the treatment over a period of time using the gene expression value.

In another embodiment, a system that is integrated for patient treatment, analysis, diagnosis and prognosis are provided for the treatment. In another embodiment, a personalized medical card may be used (with data storage capacity) for each specific patient (subject) that can provide his or her disease diagnosis gene expression value for a portfolio of genes, treatment pattern and analysis. The data generated will be stored in each card as well as updated to the central database server. The information of each patient will be stored and shared with the insurance company, health care personal and institution that provide health care.

In another embodiment, the gene expression value is analyzed using a penalized discriminate analysis with recursive feature elimination. This disclosure particularly describes cancer diagnosis and treatment for an individual.

A method of diagnosing a cancer in a mammalian subject includes the steps of examining a sample containing the subject's samples and detecting a variance in the gene expression values for the portfolio of genes that are statistically significant in number, e.g., at least 10 (not limited to) tumor and non-tumor genes from those same genes in a characteristic disease or healthy gene expression value. A significant variance in the gene expression value of these genes when compared to an average gene expression value profile of a normal control, or significant similarities to an average gene profile of subjects with cancer, correlates with a specific type of cancer and/or the location of tumor. The present disclosure relates to a method of diagnosis and/or follow up of several types of cancer, for instance after a chemotherapy or after an operation.

In one embodiment, the method of diagnosis and/or follow up of the evolution of cancer includes the analysis of the RNA component and the mRNA coding for the proteins of the ribonucleoprotein telomerase in the blood plasma or serum.

The present disclosure accommodates the use of tissue and blood for gene expression value analysis but not limited to archived paraffin-embedded biopsy material, aspirates, fine needle aspirates, and any biological sample from mammalian subject for assay of all marker in the set. It is also compatible with several different methods of tumor tissue harvest, for example, via core biopsy or fine needle aspiration. Further, for each member of the portfolio of genes, the disclosure specifies oligonucleotide sequences that can be used in the test.

In one embodiment, a method of diagnosing cancer is performed by identifying differential modulation of each gene (relative to the expression value of the same genes in a normal population) in a combination of portfolio of genes comprising of pathology associated pathways.

Accordingly, in one embodiment a linear sequence of a polynucleotide comprising a selected from the portfolio of genes (10-45 nucleotides long) comprises of TRP channel encoding genes, Breast cancer encoding genes such as HER-2 and its subtypes. Preferably, said RNA is overabundant in a proportion of breast cancer cells. In one embodiment, of this disclosure is an isolated polynucleotide comprising a linear sequence is represented by SEQ. ID NO: 01 to SEQ. ID NO: 061. These embodiments include an isolated polynucleotide which is a DNA polynucleotide, an RNA polynucleotide, a polynucleotide probe, or a polynucleotide primer.

In one embodiment, the RNA is overabundant by at least about 20% of a representative panel of breast cancer cell lines; more preferably, it is overabundant by at least about 40% of the panel; even more preferably, it is overabundant by at least 60% or more. In a further embodiment, RNA is isolated from a fixed, wax-embedded breast cancer tissue specimen of the patient.

In a different aspect, the disclosure concerns a method of preparing a personalized genomics profile for a patient, comprising the steps of:
  (a) subjecting RNA extracted from a breast tissue obtained from the patient to gene expression analysis;
  (b) determining the expression level of one or more genes selected from the breast cancer genes, wherein the expression level is normalized against a control gene or genes and optionally is compared to the amount found in a breast cancer reference tissue set; and (c) creating a report summarizing the data obtained by the gene expression analysis. (d) storing the data and sharing it with the stake holders such as physicians, insurance companies and hospitals.

In one embodiment, a method of diagnosing breast cancer cells is disclosed. Still another embodiment of this disclosure is a diagnostic kit for detecting or measuring specific gene expression value present in clinical samples; comprising a reagent, and a buffer in suitable packaging, wherein the reagent comprises of the RNAse inhibitor, TRIZOL™ reagent, ethanol, dNTPs, Reverse Transcriptase enzyme, stabilizing buffer solutions, DNA polymerases, SYBER green dNTPs, target polynucleotide's as primers for gene expression value analysis and magnesium chloride.

The present disclosure relates to the diagnosis of cancer, and more specifically to the identifying and measuring the portfolio of gene expressed by circulating cells of the immune system and/or circulating cancer cells and/or tumor cells. In one embodiment, identification of differentially modulated gene (relative to the expression value of the same genes in a normal population) is performed using a combination of genes selected from the group comprising of SEQ ID NO: 001 to 061.

Yet another embodiment, the gene expression value of the immune cell from the peripheral blood is used as a diagnostic parameter to predict the disease state.

DETAILED DESCRIPTION

The instant disclosure describes a method, a system and a kit for diagnosing and treating various disease conditions using the gene expression value in an individual. The present disclosure describes a novel method for the diagnosis of cancer based on gene expression value for a given portfolio of genes.

Figure 1:
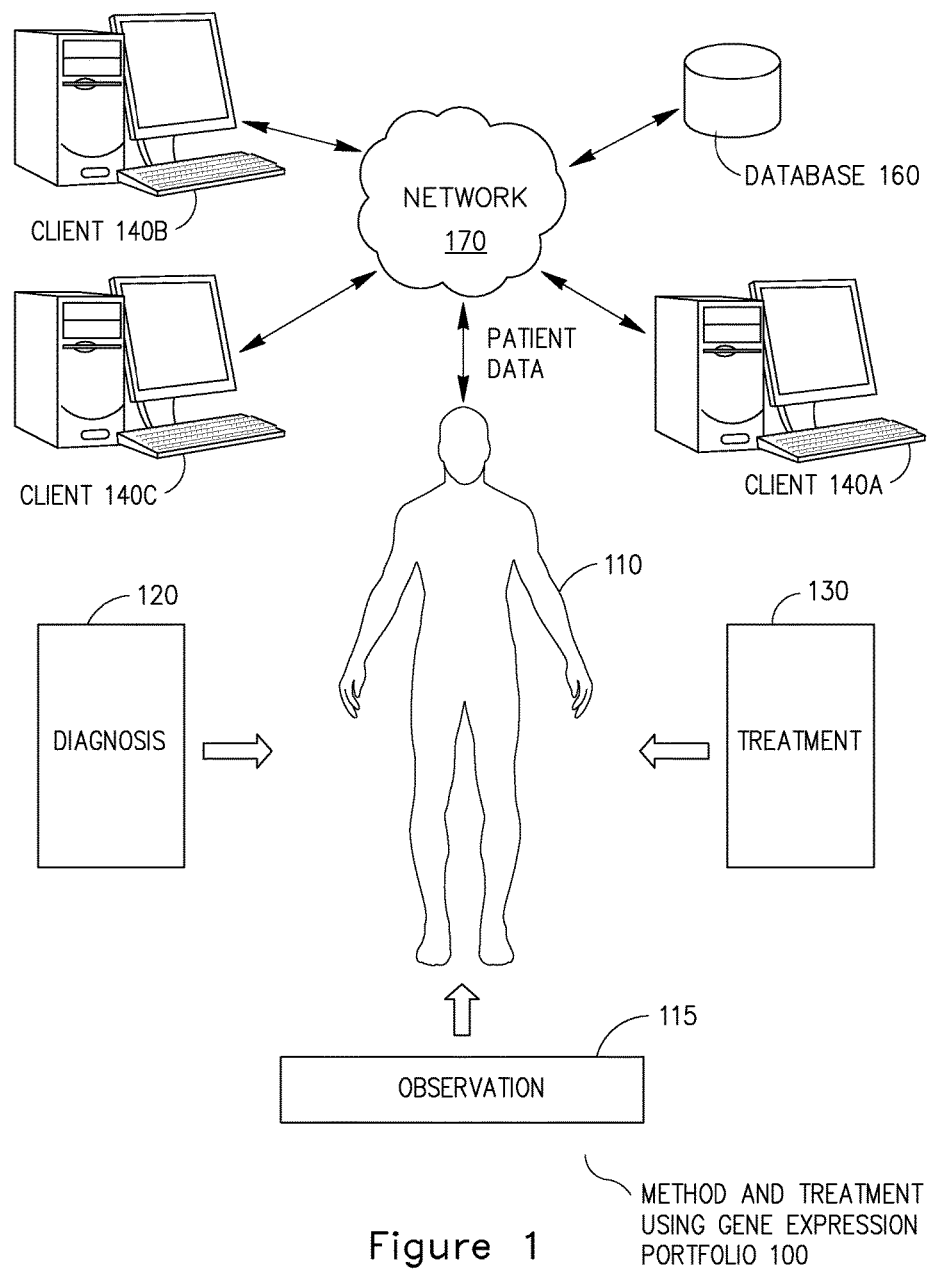
FIG. 1 shows a method and treatment using gene expression value 100 to treat a subject having cancer.

FIG. 1, shows an individual 110 having a disease condition that is being diagnosed 120 using the gene expression value after the physician or the medical care personal has accessed the background and performed routine clinical tests. Suitable treatment 130 is performed using the conventional method or proposed treatment 400. The medical data thus produced is stored in a personalized card 180. A system comprising of several client servers 140A . . . N is used for accessing, storing, analyzing and prescribing the medical treatment for the individual 110. The data is stored in database 160 for future use. The current system is portable and may be used for electronic medical record keeping and updating other information such as personal identification number, medical record number, physical check up data etc.

Figure 2:
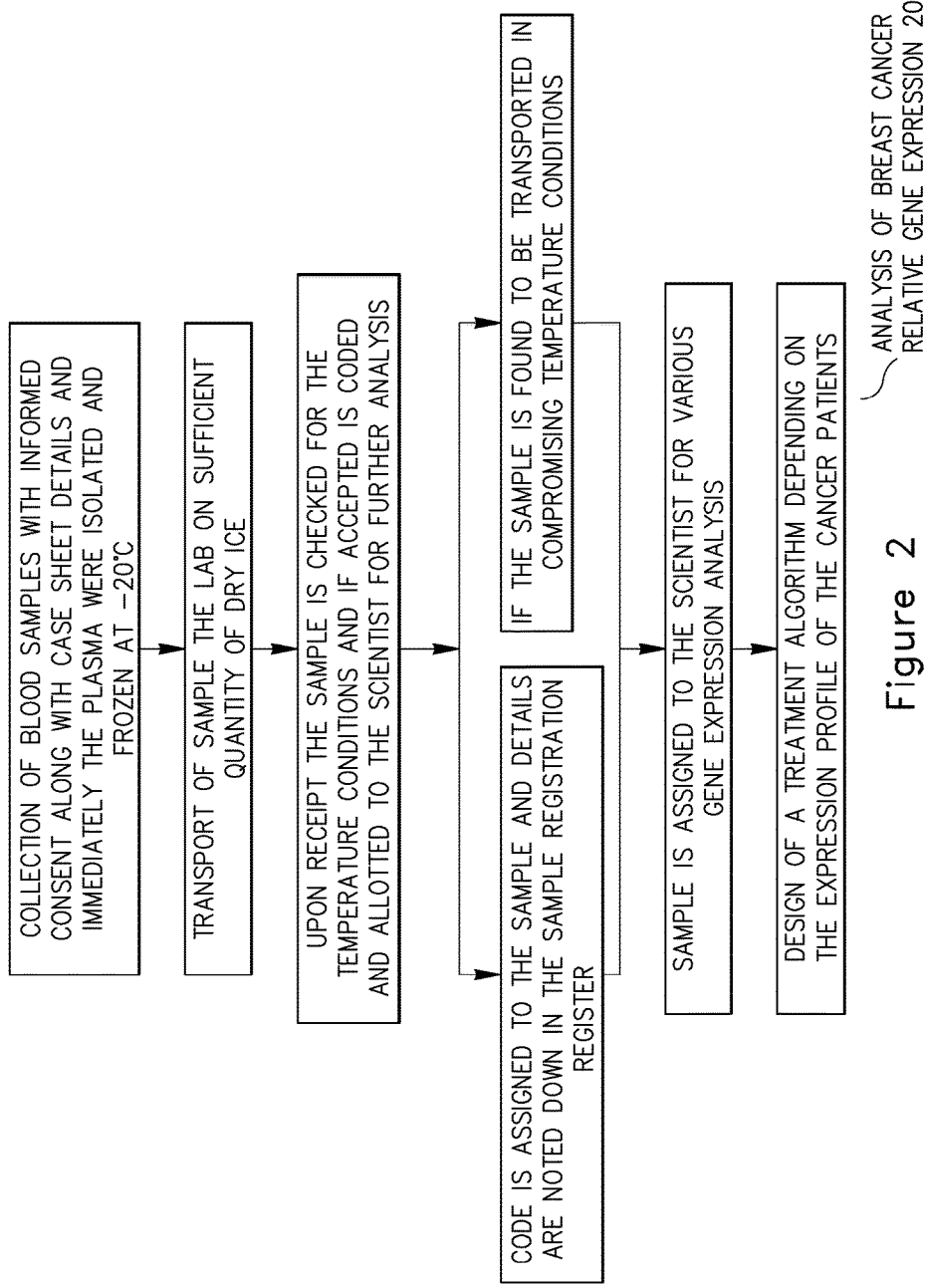
FIG. 2 shows a flow chart of analysis of breast cancer relative gene expression 200.

FIG. 2, shows a flow chart for the treatment method. The treatment method may involve the analysis of an array of gene expression value for a portfolio of genes from a biological sample of one or more subjects having the disease in question by applying penalized discriminant analysis and recursive feature elimination steps to the gene expression value.

The recursive feature elimination identifies and eliminates the least informative up-regulated and down-regulated genes from the first profile. These steps are optionally repeated until a gene expression value profile is obtained containing statistically significant number of genes that vary in expression value from the expression value of the same genes in the array of the healthy or disease control. This gene expression value profile is a characteristic of the selected disease, disorder or genetic pathology or a stage of the selected disease, disorder or genetic pathology. The profile of variance in expression value of the genes compared to a normal control or to a disease control correlates with the type and/or location of the disease, disorder or genetic pathology.

In one embodiment, the gene expression value profiles of the immune cells circulating in the peripheral blood of cancer patients reflect the presence of a solid tumor. Preferably, for cancer characterized by a solid tumor, the genes examined for the profiles are genes normally expressed by the patients' immune cells. For cancer in which the tumor or cancer cells circulate in the peripheral blood, e.g., CTCL, is a specific example of cancer or tumor now present in circulating in blood.

Each gene is sufficiently specific to indicate the type and location of the cancer or tumor. In some embodiments, this characteristic gene expression value is detectable earlier than any other sign of tumor presence. Gene expression value for portfolio of genes to be detected in peripheral blood samples thus is a powerful tool for cancer diagnosis and staging, as well as the monitoring of therapeutic efficacy.

In one embodiment, for establishing gene expression value for portfolio of gene profile includes determining the amount of RNA that is produced by a gene that can code for a protein or peptide. This is accomplished by using methods such as reverse transcriptase PCR (RT-PCR), competitive RT-PCR, real time RT-PCR, differential display RT-PCR, Northern Blot analysis and other related tests.

In one embodiment, a portfolio of genes may be designed in such a way that they are clinically relevant for making a diagnosis, prognosis, or treatment choice. These sets of genes make up the portfolio of genes for the disclosure.

Genes that display similar expression value patterns may be co-regulated by an identical factor that regulates the genes in the same direction. Choosing an optimal portfolio of genes is beneficial for providing a sensitive and accurate diagnostic kit.

In the method of the disclosure, a group of genetic marker is selected for use in diagnostic applications. These groups of marker are "portfolios". Diagnostic applications include the detection or identification of a disease state or condition of a subject, determining the likelihood that a subject will may suffer from a disease or condition, determining the likelihood that a subject with a disease or condition will respond to therapy, determining the prognosis of a subject with a disease or condition (or its likely progression or regression), and determining the effect of a treatment on a subject with a disease or condition. For example, the method can be used to establish portfolios for detecting the presence or likelihood of a subject contracting colon cancer or the likelihood that such a subject will respond favorably to cytotoxic drugs.

The portfolio of gene selected by the method of the disclosure contain a number and type of marker that assure accurate and precise results and are economized in terms of the number of genes that comprise the portfolio.

Most preferably, the markers employed in the portfolio are nucleic acid DNA Sequences that express mRNA ("genes"). Expression value of the marker may occur ordinarily in a healthy subject and be more highly expressed or less highly expressed when an event that is the object of the diagnostic application occurs. Alternatively, expression value may not occur except when the event that is the object of the diagnostic application occurs.

Distinctions are made among the diagnostic parameters through the use of mathematical/statistical values that are related to each other. The preferred distinctions are mean signal readings indicative of gene expression value and measurements of the variance of such readings.

A relationship between each genes baseline and experimental value must first be established. The preferred process is conducted as follows. A baseline class is selected. Typically, this will comprise of genes from a population that does not have the condition of interest. For example, if one were interested in selecting a portfolio of genes that are diagnostic for breast cancer, samples from patients without breast cancer can be used to make the baseline class. Once the baseline class is selected, the arithmetic mean and standard deviation is calculated for the indicator of gene expression value of each gene for baseline class samples.

Definitions

"Patient" or "subject" as used herein means a mammalian animal, including a human, a veterinary or farm animal, a domestic animal or pet, and animals normally used for clinical research.

"Sample" as used herein means any biological fluid or tissue that contains immune cells and/or cancer cells. A suitable sample for use in this disclosure, whether the cancer is a solid tumor cancer or a cancer characterized by circulating cancer cells, includes peripheral blood. Other useful biological samples include, without limitation, fine needle aspirants, parafilm embedded tissue, whole blood, saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a patient having cancer. Such samples may further be diluted with saline, buffer or physiologically acceptable diluents. Alternatively, such samples are concentrated by conventional means.

"Immune cells" as used herein means B-lymphocytes, T-lymphocytes, NK cells, macrophages, mast cells, monocytes and dendritic cells.

The term "polynucleotide," when used in singular or plural, generally refers to any polyribonucleotide or poly deoxyribonucleotide, which may be unmodified RNA or DNA or modified RNA or DNA. Thus, for instance, polynucleotides as defined herein include, without limitation, single- and double-stranded DNA, DNA including single and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, singlestranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this disclosure, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

As used herein, the term "cancer" means any cancer. In one embodiment, the cancer is characterized by the presence of a solid tumor. Among such cancer are included, without limitation, breast cancer, neuronal cancer, prostate cancer, pancreatic cancer, brain cancer, melanoma, other skin cancer, esophageal cancer, colorectal cancer, ovarian cancer, small cell carcinoma, adrenal cancer, lung adenocarcinoma, mesothelioma, Hodgkins lymphoma and non-Hodgkins Lymphoma without blood involvement. In another embodiment, the cancer is characterized by the presence of circulating cancer cells in the peripheral blood, e.g., CTCL, T-ALL, B-ALL, CML, CLL, APL, AML, B-CLL, or hairy cell leukemia. Suitable cancer for diagnosis or screening with the methods described below include early stage cancer or late stage cancer.

By "non-tumor genes" as used herein is meant genes which are normally expressed in other cells, preferably immune cells, of a healthy mammal, and which are not specifically products of tumor cells.

The term "statistically significant number of genes" in the context of this disclosure differs depending on the degree of change in gene expression value observed. The degree of change in gene expression value varies with the type of cancer and with the size or spread of the cancer or solid tumor. The degree of change also varies with the immune response of the individual and is subject to variation with each individual. For example, in one embodiment of this disclosure, a large change, e.g., 2-3 fold increase or decrease in a small number of genes, e.g., in from 5 to 8 characteristic genes, is statistically significant. In another embodiment, a smaller relative change in about 30 or more genes is statistically significant. This is particularly true for cancer with solid tumors. Still alternatively, if a single gene is profiled as up-regulated or expressed significantly in cells which normally do not express the gene such up-regulation of a single gene may alone be statistically significant. Conversely, if a single gene is profiled as down regulated or not expressed significantly in cells which normally do express the gene, such down-regulation of a single gene may alone be statistically significant.

As an example, a single gene, which is expressed about the same in all members of a population of patients, is 4-fold down regulated in only 1% of individuals without cancer. Four such independently regulated genes in one individual, all 4 fold down regulated, would occur by chance only one time in 100 million. Therefore those 4 genes are a statistically significant number of genes for that cancer. Alternatively, if normal variance is higher, e.g., one healthy person in 10 has the gene 4-fold down-regulated, and then a larger panel of genes is required to detect variance for a particular cancer.

Thus, the methods of this disclosure contemplate examination of the expression value profile of a "statistically significant number of genes" ranging from 1 to 100 genes in a single profile. In one embodiment, the gene profile is formed by a statistically significant number of at least one gene. In another embodiment, the gene profile is formed by a statistically significant number of at least 4 genes. In still another embodiment' the gene profile is formed by at least 10 genes. In still other embodiments, the gene profiles examined as part of these methods, particularly in cases in which the cancer are characterized by solid tumors, contain, as statistically significant numbers of genes, 20, 30, 40, 50, 60, 70, 80, or 90 genes in a panel.

The following table shows an optimized portfolio of genes for Leukemia.

TABLE 1

| Acute lymphoblastic leukemia (ALL) (alteration in the gene/gene expression value) | Acute myeloid leukemia (AML) (alteration in the gene/gene expression value) | Chronic lymphocytic leukemia (CLL) (alteration in the gene/gene expression value) | Chronic myeloid leukemia (CML) (alteration in the gene/gene expression value) |
|---|---|---|---|
| (precursor B lymphoblastic leukemia) BCR-ABL (translocation) MLL (rearrangement] E2A-PBX1 (translocation) c-MYC (translocation) TEL-AML1 | FLT3 (mutation) c-KIT (mutation) N-ras (mutation) K-ras (mutation) PML-RAR alpha (translocation) AML1-ETO | Bcl-2 (overexpression value) p53 (mutation) ATM (germline and somatic mutation) Fas (absent) | BCR-ABL (translocation) EVI1 (overexpression value) AML1 (translocation) JAK2(translocation) p16/INK4A |

TABLE 1-continued

| Acute lymphoblastic leukemia (ALL) (alteration in the gene/gene expression value) | Acute myeloid leukemia (AML) (alteration in the gene/gene expression value) | Chronic lymphocytic leukemia (CLL) (alteration in the gene/gene expression value) | Chronic myeloid leukemia (CML) (alteration in the gene/gene expression value) |
|---|---|---|---|
| (translocation) (precursor T lymphoblastic leukemia) NOTCH1 (mutation) TAL1 (overexpression value) LYL1 (expression value) MLL-ENL (translocation) HOX11 (translocation) MYC (translocation) LMO2 (translocation) HOX11L2 (translocation | (translocation) PLZF-RAR alpha (translocation) AML1 (mutation) C/EBPalpha (mutation) PU.1 (mutation) CBFbeta-MYH11 (inversion) | | (mutation) p53 (mutation) RB1 (mutation) |

An important aspect of the present disclosure is to use the measured expression of certain genes by breast cancer tissue to provide prognostic information. For this purpose it is necessary to correct for (normalize away) both differences in the amount of RNA assayed and variability in the quality of the RNA used. Therefore, the assay typically measures and incorporates the expression of certain normalizing genes, including well known housekeeping genes, such as GAPDH and Cyp 1. Alternatively, normalization can be based on the mean or median signal (Ct) of all of the assayed genes or a large subset thereof (global normalization approach). On a gene-by-gene basis, measured normalized amount of a patient tumor mRNA is compared to the amount found in a breast cancer tissue reference set. The number (N) of breast cancer tissues in this reference set should be sufficiently high to ensure that different reference sets (as a whole) behave essentially the same way. If this condition is met, the identity of the individual breast cancer tissues present in a particular set will have no significant impact on the relative amounts of the genes assayed. Usually, the breast cancer tissue reference set consists of at least about 30, preferably at least about 40 different FPE breast cancer tissue specimens. Unless noted otherwise, normalized expression levels for each in RNA tested tumor/patient will be expressed as a percentage of the expression level measured in the reference set. More specifically, the reference set of a sufficiently high number (e.g. 40) of tumors yields a distribution of normalized levels of each mRNA species.

The following is the portfolio of genes selected for Breast Cancer detection, prognosis or treatment.

BCR-ABL: NM_004327.3 and ABL1: NM_005157.3

TABLE 2

Primers used for analysis for the above mentioned genes:

| Seq.ID | Unique Gene ID | DNA Sequence |
|---|---|---|
| 001 | BCR1 | GCTTCTCCCTGACATCCGTG |
| 002 | ABL1 | GGCCCATGGTACCAGGAGTG |
| 003 | BCR 2 | GGAGCTGCAGATGCTGACCAAC |
| 004 | ABL2 | GTTTCTCCAGACTGTTGACTG |
| 005 | BCR3 | CGCATGTTCCGGGACAAAAGC |
| 006 | BCR 4 | CGCTCTCCCTCGCAGAACTC |
| 007 | BCRc30 | AGAGGTCCAAGGTGCCCTAC |
| 008 | BCRc31 | CGGACATCCAGGCACTGAAG |

C30 and 31 refers to the codon position of the corresponding gene

FLT3: NM_004119.2

TABLE 3

Primers used for analysis for the above mentioned gene:

| Seq.ID | Unique Gene ID | DNA Sequence |
|---|---|---|
| 009 | FLT ITD F | GCAATTTAGGTATGAAAGCCAGC |
| 010 | FLT ITD R | CTTTCAGCATTTTGACGGCAACC |
| 011 | FLT D F | CCGCCAGGAACGTGCTTG |
| 012 | FLT D R | GCAGCCTCACATTGCCCC |

PML: NM_002675.3 and RARA: NM_000964.3

TABLE 4

Primers used for analysis for the above mentioned genes:

| Seq.ID | Unique Gene ID | DNA Sequence |
|---|---|---|
| 013 | PML | ACCGATGGCTTCGACGAGTTC |
| 014 | RARA | AGCCCTTGCAGCCCTCACAG |

JAK2: NM_004972.3

TABLE 5

Primers used for analysis for the above mentioned gene:

| Seq.ID | Unique Gene ID | DNA Sequence |
|---|---|---|
| 015 | JK Forward (SP) | AGCATTTGGTTTTAAATTATGGAGTATATT |

TABLE 5-continued

Primers used for analysis for the above mentioned gene:

| Seq.ID | Unique Gene ID | DNA Sequence |
|---|---|---|
| 016 | JK Forward (IC) | ATCTATAGTCATGCTGAAAGTAGGAGAAAG |
| 017 | JK Reverse | CTGAATAGTCCTACAGTGTTTTCAGTTTCA |

P53: NM_000546.4

TABLE 6

Primers used for analysis for the above mentioned genes are:

| Seq.ID | Unique Gene ID | DNA Sequence |
|---|---|---|
| 018 | TP53FW | GGCCCACTTCACCGTACTAA |
| 019 | TP53RE | GTGGTTTCAAGGCCAGATGT |

EVI1, NM_001105077.3

TABLE 7

Primers used for analysis for the above mentioned gene:

| S.No. | Unique Gene ID | DNA Sequence |
|---|---|---|
| 020 | EVI1 F | CAAGGAAACTGGCCACAAAT |
| 021 | EVI1 R | GGGGCTTTGTAAGGAGAACC |

A set of portfolio of genes optimized for breast cancer detection are as follows: BRCA1, BRCA2, MET, PR, PIK3A, EGFR, PTEN, BRAF, kRAS, Her2, ESR1.

BRCA1: NM_007295.2

TABLE 8

Primers used for analysis for the above mentioned gene:

| Seq. ID | Unique Gene ID | DNA Sequence |
|---|---|---|
| 022 | BRCA1Fw | TGCTTGAAGTCTCCCTTG |
| 023 | BRCA1Re | CTTCCATTGAAGGGTCTG |

BRCA2: NM_138081.2

TABLE 9

Primers used for analysis for the above mentioned gene:

| Seq. ID | Unique Gene ID | DNA Sequence |
|---|---|---|
| 024 | BRCA2Fw | ACCCTTTCAGGTCTAAATGG |
| 025 | BRCA2Re | TGCCTGCTTTACTGCAAG |

MET: NM_078571.2

TABLE 10

Primers used for analysis for the above mentioned gene:

| Seq.ID | Unique Gene ID | DNA Sequence |
|---|---|---|
| 026 | MET Fw | GAAGACCTTCAGAAGGTTG |
| 027 | MET Re | TGGGGAGAATATGCAGTG |

PR: NM_001172044.1

TABLE 11

Primers used for analysis for the above mentioned gene:

| Seq. ID | Unique Gene ID | DNA Sequence |
|---|---|---|
| 028 | PR-Fw | GGACTTGTGAGTACTCTG |
| 029 | PR-Re | AGTGGGTGTTGAATGTG |

PI3KA: NM_06218.2

TABLE 12

Primers used for analysis for the above mentioned gene:

| Seq. ID | Unique Gene ID | DNA Sequence |
|---|---|---|
| 030 | PI3KA Fw | GGACAATCGCCAATTCAG |
| 031 | PI3KA Re | TGGTGGTGCTTTGATCTG |

EGFR: NM_057410.3

TABLE 13

Primers used for analysis for the above mentioned gene:

| Seq. ID | Unique Gene ID | DNA Sequence |
|---|---|---|
| 032 | EGFR Fw | TTAGCAGGAAAGGCACTG |
| 033 | EGFR Re | CAGCTTCATCCTACACAAG |

PTEN: NM_058074.3

TABLE 14

Primers used for analysis for the above mentioned gene:

| Seq. ID | Unique Gene ID | DNA Sequence |
|---|---|---|
| 034 | PTEN Fw | GACAGACTGATGTGTATACG |
| 035 | PTEN Re | GTGTAAATAGCTGGAGATGG |

BRAF: NM_139294.5

TABLE 15

Primers used for analysis for the above mentioned gene:

| Seq. ID | Unique Gene ID | DNA Sequence |
|---|---|---|
| 036 | BRAF Fw | ATGGTGATGTGGCAGTGAAA |
| 037 | BRAF Re | TAGCCAGTTGTGGCTTTGTG | kRAS: NM_021284.6

TABLE 16

Primers used for analysis for the above mentioned gene:

| Seq. ID | Unique Gene ID | DNA Sequence |
|---|---|---|
| 038 | kRAS Fw | AGGGCAGTTTGGATAGCTCA |
| 039 | kRAS Re | CACCACCCCAAAATCTCAAC |

Her2: NM_131089.1

TABLE 17

Primers used for analysis for the above mentioned gene:

| Seq. ID | Unique Gene ID | DNA Sequence |
|---|---|---|
| 040 | Her2Fw | AGTACCTGGGTCTGGACGTG |
| 041 | Her2Re | CTGGGAACTCAAGCAGGAAG |

ESR1: NM_012689.1

TABLE 18

Primers used for analysis for the above mentioned gene:

| Seq. ID | Unique Gene ID | DNA Sequence |
|---|---|---|
| 042 | ESR1Fw | CTTGTGCAGGATTGTTGTG |
| 043 | ESR1Re | GCCAATTGTAGGAACACAG |

The following is the portfolio of genes selected are for brain cancer detection: TW, EMP3, OLIG2, IGFBP2, LGALS3, AQP1, TP53, EVI1, IL3

TW: NM_022093.1

TABLE 19

Primers used for analysis for the above mentioned gene:

| Seq. ID | Unique Gene ID | DNA Sequence |
|---|---|---|
| 044 | TW Fw | CTGTCCTGGGCAGAAAGAAG |
| 045 | TW Re | GGTGAGAGGGAAGGAACCTC |

EMP3: NM_001425.2

TABLE 20

Primers used for analysis for the above mentioned gene:

| Seq. ID | Unique Gene ID | DNA Sequence |
|---|---|---|
| 046 | EMP3 Fw | GAGAGCGAGCGAGAGAGAAA |
| 047 | EMP3 Re | GCTGGAGTCGGAGTCTTGTC |

OLIG2: NM_005806.2

TABLE 21

Primers used for analysis for the above mentioned gene:

| Seq. ID | Unique Gene ID | DNA Sequence |
|---|---|---|
| 048 | OLIG2Fw | CAGAAGCGCTGATGGTCATA |
| 049 | OLIG2Re | TCGGCAGTTTTGGGTTATTC |

IGFBP2: NM_000597.2

TABLE 22

Primers used for analysis for the above mentioned gene:

| Seq. ID | Unique Gene ID | DNA Sequence |
|---|---|---|
| 050 | IGFBP2 Fw | GCAGAAAACGGAGAGTGCTT |
| 051 | IGFBP2 Re | AAAGCAAGAAGGAGCAGGTG |

LGALS3: NM_002306.3

TABLE 23

Primers used for analysis for the above mentioned gene:

| Seq. ID | Unique Gene ID | DNA Sequence |
|---|---|---|
| 052 | LGALS3 Fw | GGCCACTGATTGTGCCTTAT |
| 053 | LGALS3 Re | TCTTTCTTCCCTTCCCCAGT |

AQP1: NM_001185060.1

TABLE 24

Primers used for analysis for the above mentioned gene:

| Seq.ID | Unique Gene ID | DNA Sequence |
|---|---|---|
| 054 | AQP1 Fw | ATTAACCCTGCTCGGTCCTT |
| 055 | AQP1 Re | ACCCTGGAGTTGATGTCGTC |

TP53: NM_030989.3

TABLE 25

Primers used for analysis for the above mentioned gene:

| Seq. ID | Unique Gene ID | DNA Sequence |
|---|---|---|
| 056 | P53 Fw | GGCCCACTTCACCGTACTAA |
| 057 | P53 Re | GTGGTTTCAAGGCCAGATGT |

EVI1: NM_001105077.3

TABLE 26

Primers used for analysis for the above mentioned gene:

| Seq. ID | Unique Gene ID | DNA Sequence |
|---|---|---|
| 058 | EVI1 Fw | CAAGGAAACTGGCCACAAAT |
| 059 | EVI1 Re | GGGGCTTTGTAAGGAGAACC |

IL3: NM_000588.3

TABLE 27

Primers used for analysis for the above mentioned gene:

| Seq. ID | Unique Gene ID | DNA Sequence |
|---|---|---|
| 060 | I13 Fw | CTTTGCCTTTGCTGGACTTC |
| 061 | I13 Re | CCGTCCTTGATATGGATTGG |

After the forward (Fw) and reverse (Re) primer design for each portfolio of genes selected the next step is to extract total RNA extraction and the following protocol was used. Mix 0.75 ml of TRI Reagent RT—Blood with 0.25 ml of whole blood, plasma or serum. Close the tube and shake the resulting lysate by hand or vortex. Supplement the homogenate with 50 µl of chloroform per 0.75 ml of TRI Reagent RT—Blood used for lysis. Cover the samples tightly and shake vigorously for 15 seconds. Centrifuge the resulting mixture at 12,000 g for 15 minutes at 4 C. Following centrifugation, the mixture separates into a lower, red phenol phase, the interphase, and the upper aqueous phase. RNA remains in the aqueous phase whereas DNA and proteins are in the interphase and organic phase. Transfer 0.5 ml of the aqueous phase to a fresh tube. Precipitate RNA from the aqueous phase by mixing it with 0.5 ml of isopropanol. Store samples at room temperature for 5-10 minutes and centrifuge at 4,000-12,000 g for 5 minutes at 4-25 C. Remove the supernatant and wash the RNA pellet with 1 ml of 75% ethanol by vortexing and subsequent centrifugation at 6,000 g for 5 minutes at 4-25 C. Remove the ethanol wash and add water to the RNA pellet. Avoid drying the pellet as this will decrease its solubility.

Once the total RNA is extracted the first step is to perform cDNA amplification, which is done as follows:

STEP 1

Reaction mix I for cDNA amplification.

| Step | | |
|---|---|---|
| 1 | Total RNA (1 ng-1 µg) | 1-10 µl |
| 1 | Random primer (50 pm/µl) | 2 µl |
| 2 | dNTPs (10 mM) | 4 µl |
| 3 | Total volume | 16 µl |
| 4 | Incubate the reaction at 70° C. for 5 min | |

Add the following to the reaction mix II into Reaction mix 1 to perform:

STEP 2

Reaction mix II for cDNA amplification

| 1x Reaction buffer | 2 µl |
|---|---|
| 100 U/µl RNAse inhibitor | 1 µl |
| 1 unit of Reverse transcriptase | 1 µl |
| Total volume | 4 µl |

Mix Reaction I and II well by pipetting and setup the reverse transcription reaction and perform Step 3.

STEP 3

Thermal cycling conditions for cDNA amplification (reverse transcription)

| Cycle No | Temperature and time |
|---|---|
| 1 | 25° C. for 10 min |
| 2 | 42° C. for 60 min |
| 3 | 95° C. for 5 min |

Real time PCR analysis: Add appropriate gene specific primers with prepared cDNA and subject to RT-PCR. Real time PCR mix contains cDNA 1 µl, Forward primer (10 µm/µl) 0.4 µl, Reverse Primer (10 µm/µl) 0.4 µl, EvaGreen Mix (2×), 12.5 µl, H2O 5.7 µl, and the total volume would be 20 µl.

Figure 3:
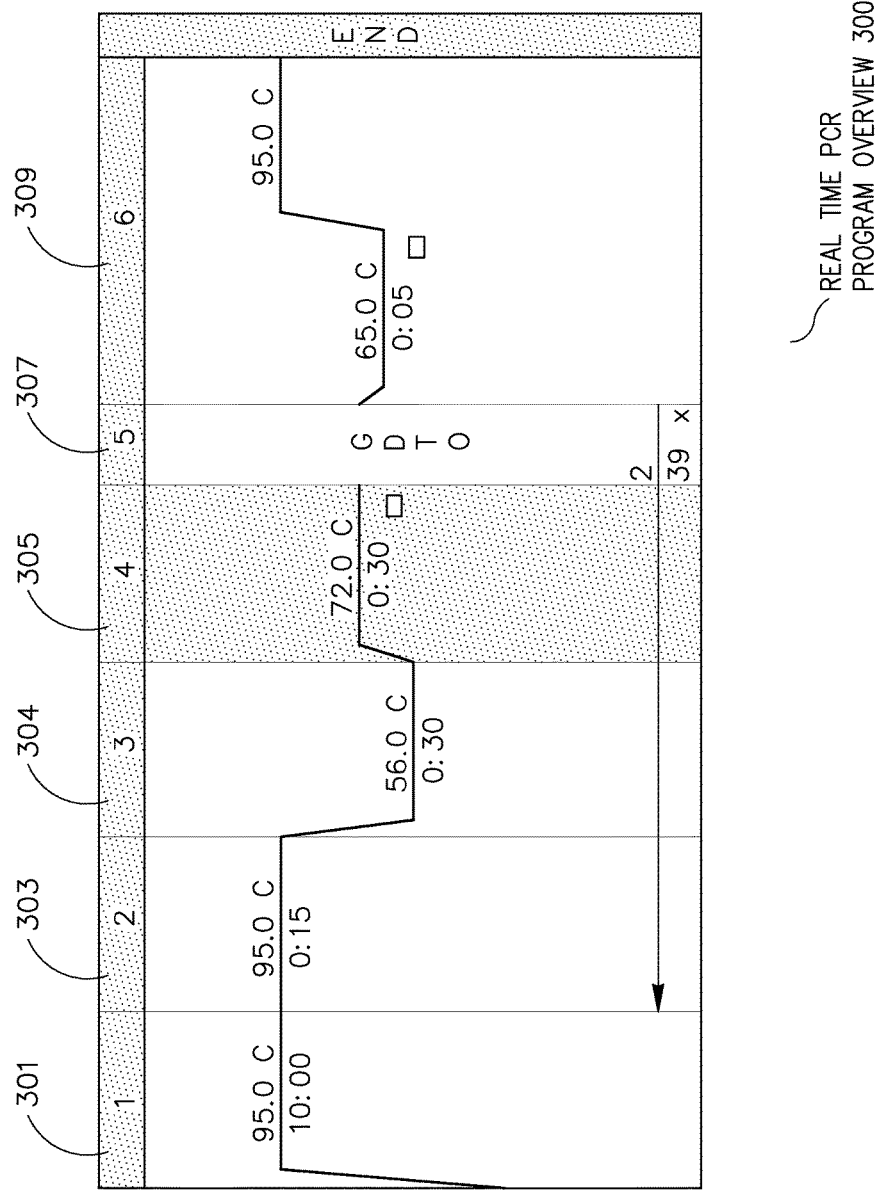
FIG. 3 shows real time PCR program overview 300 for one of the RT-PCR reaction.

Real time PCR condition, also shown in FIG. 3. The cycle number 3 is X° C. and it depends on the primer being used and their respective annealing temperature.

Portfolio of Genes, their amplified product and their respective annealing temperature.

TABLE 28

| Marker Name | Forward Primer | Reverse Primer | Amplified Product Size | Ann Temp |
|---|---|---|---|---|
| BRCA2 | ACCCTTTCAGGTCT AAATGG | TGCCTGCTTTACTG CAAG | 268 | 54 |
| MET | GAAGACCTTCAGAA GGTTG | TGGGGAGAATATGC AGTG | 267 | |
| PR | GGACTTGTGAGTAC TCTG | AGTGGGTGTTGAAT GTG | 266 | 57 |
| PIK3AF | GGACAATCGCCAAT TCAG | TGGTGGTGCTTTGA TCTG | 268 | |
| BRCA1 | TGCTTGAAGTCTCC CTTG | CTTCCATTGAAGGG TCTG | 267 | 58 |
| EGFR | TTAGCAGGAAAGGC ACTG | CAGCTTCATCCTAC ACAAG | 269 | |
| PTEN | GACAGACTGATGTG TATACG | GTGTAAATAGCTGG AGATGG | 269 | |
| BRAF | ATGGTGATGTGGCA GTGAAA | TAGCCAGTTGTGGC TTTGTG | 150 | |
| ESR1 | CTTGTGCAGGATTG TTGTG | GCCAATTGTAGGAA CACAG | 269 | 68 |
| NHer 2 | AGTACCTGGGTCTG GACGTG | CTGGGAACTCAAGC AGGAAG | 194 | 51 |
| NkRAS | AGGGCAGTTTGGAT AGCTCA | CACCACCCCAAAAT CTCAAC | 153 | |

Observation in the Change of Gene Expression Value and its Significance

The breast cancer gene expression value profile is characterized by analyzing the hereditary genes such as BRCA1 and also the target oncogenes relative gene expression value pattern involved in the oncogenesis and metastasis.

BRCA1 Gene Expression Value Analysis

The breast cancer hereditary gene BRCA1 relative gene expression value in the patients sample is analyzed using RT-PCR and is compared with the house keeping gene, GADPH. The amplification details were provided in the following table:

TABLE 29

| Patient | Sample Name | Ct Value 1 | Ct Value 2 | Mean | Sample Name | Ct Value 1 | Ct Value 2 | Mean | Delta Ct |
|---|---|---|---|---|---|---|---|---|---|
| 1 | BRCA1-Samp1 | 28.01 | 28.03 | 28.02 | GAPDH-Samp1 | 25.25 | 25.28 | 25.265 | 2.755 |
| 2 | BRCA1-Samp2 | 26.51 | 26.18 | 26.345 | GAPDH-Samp2 | 24.36 | 24.33 | 24.345 | 2 |
| 3 | BRCA1-Samp3 | 26.04 | 25.18 | 25.61 | GAPDH-Samp3 | 23.53 | 23.38 | 23.455 | 2.155 |
| 4 | BRCA1-Samp4 | 24.89 | 25.11 | 25 | GAPDH-Samp4 | 23.4 | 23.36 | 23.38 | 1.62 |

TABLE 30

| | delta delta Ct | 2 power delta.delta Ct |
|---|---|---|
| Patient 1 | −0.93 | 0.524858342 |
| Patient 2 | −1.685 | 0.311002913 |
| Patient 3 | −1.53 | 0.346277367 |
| Patient 4 | −2.065 | 0.238986329 |

Cancer Gene Specific Analysis

The specific breast cancer genes relative gene expression value in the patients and control sample is analyzed using RT-PCR and is compared with the house keeping gene, GADPH. The amplification details were provided in the following table:

TABLE 31

| Sample Name | Ct Value 1 | Ct Value 2 | Mean | Sample Name | Ct Value 1 | Ct Value 2 | Mean | Delta Ct |
|---|---|---|---|---|---|---|---|---|
| EGFR-Patient 1 | 33.79 | 33.67 | 33.73 | GAPDH-Patient 1 | 24.55 | 25.03 | 24.79 | 8.94 |
| PTEN-Patient 1 | 29.68 | 29.23 | 29.46 | | | | | 4.665 |
| BRAF-Patient 1 | 23.3 | 24.52 | 23.91 | | | | | −0.88 |
| EGFR-Patient 2 | 28.68 | 27.6 | 28.14 | GAPDH-Patient 2 | 24.27 | 23.15 | 23.71 | 4.43 |
| PTEN-Patient 2 | 27.1 | 26.85 | 26.98 | | | | | 3.265 |
| BRAF-Patient 2 | 23.33 | 21.24 | 22.29 | | | | | −1.425 |
| EGFR-Patient 3 | 28.17 | 26.43 | 27.3 | GAPDH-Patient 3 | 20.78 | 20.77 | 20.78 | 6.525 |
| PTENPatient 3 | 26.34 | 26.41 | 26.38 | | | | | 5.6 |
| BRAF-Patient 3 | 22.3 | 22.74 | 22.52 | | | | | 1.745 |
| EGFR-Sample4 | 27.45 | 27.98 | 27.72 | GAPDH-Sample4 | 21.05 | 20.95 | 21 | 6.715 |
| PTENSample4 | 27.04 | 27.11 | 27.08 | | | | | 6.075 |
| BRAFSample4 | 22.05 | 22.26 | 22.16 | | | | | 1.155 |

TABLE 32

| Sample Name | Ct Value 1 | Ct Value 2 | Mean | Delta Ct |
|---|---|---|---|---|
| Control-EGFR | 32.36 | 29.11 | 30.74 | 9.885 |
| Control-PTEN | 25.33 | 25.4 | 25.37 | 4.515 |
| Control-BRAF | 21.2 | 21.47 | 21.34 | 0.485 |
| Control-GAPDH | 20.79 | 20.91 | 20.85 | |

TABLE 33

| Sample Name | Ct Value 1 | Ct Value 2 | Mean | Sample Name | Ct Value 1 | Ct Value 2 | Mean | Delta Ct |
|---|---|---|---|---|---|---|---|---|
| Patient 3-Her2 | 29.54 | 29.54 | 29.54 | Patient 3-GAPDH | 24.6 | 24.28 | 24.44 | 5.1 |
| Patient 3-kRAS | 21.05 | 21.34 | 21.2 | | | | | −3.245 |
| Her2-Patient 4 | 29.56 | 29.84 | 29.7 | Sample4-GAPDH | 23.95 | 30.03 | 26.99 | 2.71 |
| kRAS-Patient 4 | 21.86 | 22.99 | 22.43 | | | | | −4.565 |

TABLE 34

| Sample Name | Ct Value 1 | Ct Value 2 | Mean | Delta Ct |
|---|---|---|---|---|
| Control-Her2 | 23.28 | 23.71 | 23.495 | 2.35 |
| Control-kRAS | 21.07 | 21.7 | 21.385 | 0.24 |
| Control-GAPDH | 21.13 | 21.16 | 21.145 | |

Relative Gene Expression value Analysis: Absolute Relative quantification determines the input copy number, usually by relating the PCR signal. Relative quantification relates the PCR signal of the target transcript in a treatment group to that of another sample such as an untreated control. The 2(-Delta Delta C(T)) method is a convenient way to analyze the relative changes in gene expression value from real-time quantitative PCR experiments.

TABLE 35

| | | delta delta Ct | 2 power delta delta Ct |
|---|---|---|---|
| EGFR | Patient 1 | −0.945 | 0.52 |
| | Patient 2 | 0.15 | 1.11 |
| | Patient 3 | −1.365 | 0.39 |
| | Patient 4 | −3.17 | 0.11 |
| PTEN | Patient 1 | 0.15 | 1.11 |
| | Patient 2 | −1.25 | 0.42 |
| | Patient 3 | 1.085 | 2.12 |
| | Patient 4 | 1.56 | 2.95 |
| BRAF | Patient 1 | −1.365 | 0.39 |
| | Patient 2 | −1.91 | 0.27 |
| | Patient 3 | 1.26 | 2.39 |
| | Patient 4 | 0.67 | 1.59 |
| Her2 | Patient 3 | 2.75 | 6.73 |
| | Patient 4 | 0.36 | 1.28 |
| kRAS | Patient 3 | −3.485 | 0.09 |
| | Patient 4 | −4.805 | 0.04 |

Gene Expression in Breast Tumor Analysis

A gene expression study was designed and conducted with the primary goal to molecularly characterize gene expression in Biopsy or Parafilm embedded tissue samples of invasive breast ductal carcinoma, and to explore the correlation between such molecular profiles and disease-free survival. Further details of the embodiment will be described in the following non-limiting example.

Excise the tissue sample from the animal or remove it from storage. Remove RNA later stabilized tissues from the reagent using forceps. Determine the amount of tissue. Do not use more than 30 mg. Weighing tissue is the most accurate way to determine the amount. If using the entire tissue, place it directly into a suitably sized vessel for disruption and homogenization. If using only a portion of the tissue, cut it on a clean surface. Weigh the piece to be used, and place it into a suitably sized vessel for disruption and homogenization. Disrupt the tissue and homogenize the lysate in Buffer RLT Plus (do not use more than 30 mg tissue).

TABLE 36

Volumes of Buffer RLT Plus for tissue disruption and homogenization

| Amount of starting material | Volume of Buffer RLT Plus |
|---|---|
| <20 mg | 350 µl or 600 µl |
| 20-30 mg | 600 µl |

Disruption and homogenization using the TissueRuptor: Place the weighed (fresh, frozen, or RNA later stabilized) tissue in a suitably sized vessel. Add the appropriate volume of Buffer RLT Plus (see Table 36). Immediately disrupt and homogenize the tissue until it is uniformly homogeneous (usually 20-40 s).Centrifuge the lysate for 3 min at maximum speed. Carefully remove the supernatant by pipetting, and transfer it to a gDNA Eliminator spin column placed in a 2 ml collection tube (supplied). Centrifuge for 30 s at ≥8000×g (≥10,000 rpm). Discard the column, and save the flow-through. This step is important, as it removes insoluble material that could clog the gDNA Eliminator spin column and interfere with DNA removal. In some preparations, very small amounts of insoluble material will be present after the 3 min centrifugation, making the pellet invisible. Add 1 volume (usually 350 µl or 600 µl) of 70% ethanol to the flowthrough, and mix well by pipetting. Do not centrifuge. Proceed immediately to step 6. If some lysate was lost during homogenization and DNA removal, adjust the volume of ethanol accordingly. Transfer up to 700 µl of the sample, including any precipitate that may have formed, to an RNeasy spin column placed in a 2 ml collection tube (supplied). Close the lid gently, and centrifuge for 15 s at ≥8000×g (≥10,000 rpm). Discard the flow-through. Add 700 µl Buffer RW1 to the RNeasy spin column. Close the lid gently, and centrifuge for 15 s at ≥8000×g (≥10,000 rpm) to wash the spin column membrane. Discard the flow-through. Add 500 µl Buffer RPE to the RNeasy spin column. Close the lid gently, and centrifuge for 15 s at ≥8000×g (≥10,000 rpm) to wash the spin column membrane. Discard the flow-through. Add 500 µl Buffer RPE to the RNeasy spin column. Close the lid gently, and centrifuge for 2 min at ≥8000×g (≥10,000 rpm) to wash the spin column membrane. Place the RNeasy spin column in a new 1.5 ml collection tube (supplied). Add 30-50 µl RNase-free water directly to the spin column membrane. Close the lid gently, and centrifuge for 1 min at ≥8000×g (≥10,000 rpm) to elute the RNA. If the expected RNA yield is ≥30 µg, repeat step 11 using another 30-50 µl of RNase-free water, or using the eluate from step 11 (if high RNA concentration is required). The rest of the test steps are described in previous sections for determining the gene expression value for a given portfolio of genes. The results are disclosed below.

TABLE 37 a, b and c

Her 2 and kRAS Panel: Mean of the 3 Ct values for samples OT1, OB1 and OB3.

| Sample Name | Ct 1 | Ct 2 | Ct 3 | Mean |
|---|---|---|---|---|
| OT1-Her2 | 29 | 28.57 | 28.56 | 28.68 |
| OT1-kRAS | 28 | 28.17 | 28.06 | 28.09 |
| OB1-Her2 | 32 | 32.2 | 32.1 | 32.08 |
| OB1-kRAS | 29 | 28.56 | 28.59 | 28.66 |
| OB2-Her2 | 32 | 31.34 | 31.25 | 31.57 |
| OB2-kRAS | 28 | 28.3 | 28.36 | 28.28 |

Delta Ct value (Mean of OT1 Her2 minus Mean of OT1 GAPDH).
Delta Ct value Mean of OT1 kRAS minus Mean of OT1 GAPDH)

| Sample Name | Ct 1 | Ct 2 | Ct 3 | Mean | Delta Ct |
|---|---|---|---|---|---|
| OT1-GAPDH | 20.13 | 20.15 | 20.04 | 20.11 | 8.57 |
| | | | | | 7.99 |
| OB1 -GAPDH | 19.51 | 19.44 | 19.5 | 19.48 | 12.60 |
| | | | | | 9.18 |
| OB2-GAPDH | 18.7 | 19.38 | 19.28 | 19.12 | 12.45 |
| | | | | | 9.16 |

TABLE 37 a, b and c-continued

Her 2 and kRAS Panel: Mean of the 3 Ct values for samples OT1, OB1 and OB3.

Delta Ct value for Control Her2 (delta Ct Her2 minus Delta Ct GAPDH).
Delta Ct value for Control Her2 (delta CtkRAS minus Delta Ct GAPDH).

| Sample Name | Ct 1 | Ct 2 | Ct 3 | Mean | Delta Ct |
|---|---|---|---|---|---|
| C12-Her2 | 29.21 | 29.06 | 29.1 | 29.15 | 11.02 |
| C12-kRAS | 26.19 | 26.12 | 25.9 | 26.07 | 7.94 |
| C12-GAPDH | 18.09 | 18.07 | 18.2 | 18.13 | |

Delta Delta Ct value for OT1 sample (Delta Ct of OT1 Her2 minus Delta Ct value of Control).

| | | delta delta Ct | 2 power delta delta. delta Ct |
|---|---|---|---|
| Her 2 | OT1-Her2 | −2.45 | 5.45 |
| | OB1-Her2 | 1.58 | 0.33 |
| | OB2-Her2 | 1.44 | 0.37 |
| kRAS | OT1-kRAS | 0.04 | 0.97 |
| | OB1-kRAS | 1.24 | 0.42 |
| | OB2-kRAS | 1.22 | 0.43 |

From the above delta delta Ct values, it can be inferred that OT1 sample is over expressing Her2 as compared to the control.

TABLE 38 a, b, c, d for ER:

| Sample Name | Ct 1 | Ct 2 | Ct 3 | Mean |
|---|---|---|---|---|
| OT1-ESR1 | 27.9 | 27.14 | 27.05 | 27.36 |
| OB1-ESR1 | 31.17 | 31.24 | 30.98 | 31.13 |
| OB3-ESR1 | 30.91 | 30.41 | 30.23 | 30.52 |

| Sample Name | Ct 1 | Ct 2 | Ct 3 | Mean | Delta Ct |
|---|---|---|---|---|---|
| OT1-GAPDH | 21.44 | 21.34 | 21.28 | 21.35 | 6.01 |
| OB1-GAPDH | 20.62 | 20.53 | 20.82 | 20.66 | 10.47 |
| OB3-GAPDH | 20.55 | 20.33 | 20.43 | 20.44 | 10.08 |

| Sample Name | Ct 1 | Ct 2 | Ct 3 | Mean | Delta Ct |
|---|---|---|---|---|---|
| C12-ESR1 | 29.62 | 28.78 | 29.02 | 29.14 | 9.94 |
| C12-GAPDH | 19.25 | 19.17 | 19.17 | 19.20 | |

| | | delta delta Ct | 2 power delta. delta Ct |
|---|---|---|---|
| ER | OT1-ER | −3.93 | 15.28 |
| | OB1-ER | 0.53 | 0.69 |
| | OB2-ER | 0.14 | 0.91 |

From the above Delta Delta Ct values, it can be inferred that sample OT1 is over expressing ER.

TABLE 39 a, b, c and d for MET & BRCA2:

| Sample Name | Ct 1 | Ct 2 | Ct 3 | Mean |
|---|---|---|---|---|
| OB1-MET | 31.51 | 31.44 | 31.07 | 31.34 |
| OB1-BRCA2 | 30.51 | 31.02 | 30.76 | 30.76 |
| OB3-MET | 31.06 | 30.52 | 30.82 | 30.80 |
| OB3-BRCA2 | 30.25 | 30.09 | 33.68 | 31.34 |
| OT1-MET | 27.33 | 27.26 | 27.16 | 27.25 |
| OT1-BRCA2 | 28.37 | 28.29 | 28.44 | 28.37 |

TABLE 39 a, b, c and d-continued for MET & BRCA2:

| Sample Name | Ct 1 | Ct 2 | Ct 3 | Mean | Delta Ct |
|---|---|---|---|---|---|
| OB1-GAPDH | 20.82 | 20.64 | 20.72 | 20.73 | 10.61 |
| | | | | | 10.04 |
| OB3-GAPDH | 20.36 | 20.44 | 20.19 | 20.33 | 10.47 |
| | | | | | 11.01 |
| OT1-GAPDH | 21.37 | 21.23 | 20.96 | 21.19 | 6.06 |
| | | | | | 7.18 |

| Sample Name | Ct 1 | Ct 2 | Ct 3 | Mean | Delta |
|---|---|---|---|---|---|
| C12-MET | 30.7 | 30.58 | 30.26 | 30.53 | 11.14 |
| C12-BRCA2 | 28.6 | 28.81 | 28.8 | 28.76 | 9.37 |
| C12-GAPDH | 19.3 | 19.33 | 19.45 | 19.39 | |

| | | delta delta Ct | 2 power delta ddelta Ct |
|---|---|---|---|
| MET | OB1-MET | −0.53 | 1.44 |
| | OB3-MET | −0.67 | 1.59 |
| | OT1-MET | −5.08 | 33.82 |
| BRCA2 | OB1-BRCA2 | 0.67 | 0.63 |
| | | 1.64 | 0.32 |
| | | −2.19 | 4.56 |

From the above table, MET is being over expressed in the OT1 sample.

TABLE 39 a, b, c and d for BRCA1, EGFR, PTEN, BRAF:

| Sample Name | Ct 1 | Ct 2 | Ct 3 | Mean |
|---|---|---|---|---|
| OT1-BRCA1 | 29.51 | 29.69 | 30.04 | 29.75 |
| OT1-EGFR | 27.88 | 28.06 | 27.93 | 27.96 |
| OT1-PTEN | 28.2 | 28.3 | 28.05 | 28.18 |
| OT1-BRAF | 27.33 | 30.37 | | 28.85 |
| OB1-BRCA1 | 31.58 | 30.67 | 30.91 | 31.05 |
| OB1-EGFR | 31.91 | 31.08 | 31.66 | 31.55 |
| OB1-PTEN | 25.66 | 25.57 | 25.4 | 25.54 |
| OB1-BRAF | 26.62 | 27.14 | | 26.88 |
| OB3-BRCA1 | 30.85 | 31.35 | 31.01 | 31.07 |
| OB3-EGFR | 31.74 | 31.39 | 31.2 | 31.44 |
| OB3-PTEN | 25.43 | 25 | 25.38 | 25.27 |
| OB3-BRAF | 26.49 | 28.03 | | 27.26 |

| Sample Name | Ct 1 | Ct 2 | Ct 3 | Mean | Delta Ct |
|---|---|---|---|---|---|
| OT1-GAPDH | 21.73 | 21.53 | 21.61 | 21.62 | 8.12 |
| | | | | | 6.33 |
| | | | | | 6.56 |
| | | | | | 7.23 |
| OB1-GAPDH | 21.18 | 21.03 | 21.2 | 21.14 | 9.92 |
| | | | | | 10.41 |
| | | | | | 4.41 |
| | | | | | 5.74 |
| OB3-GAPDH | 21.19 | 21.18 | 20.93 | 21.1 | 9.97 |
| | | | | | 10.34 |
| | | | | | 4.17 |
| | | | | | 6.16 |
| C15-BRCA1 | 30.1 | 29.56 | 30.08 | 29.91 | 9.53 |
| C15-EGFR | 30.83 | 30.28 | 31.02 | 30.71 | 10.33 |
| C15-PTEN | 23.71 | 23.9 | 23.66 | 23.76 | 3.38 |
| C15-BRAF | 25.06 | 24.93 | | 25.00 | 4.62 |
| C15-GAPDH | 20.82 | 20.24 | 20.08 | 20.38 | |

| | | delta delta Ct | 2 power delta ddelta Ct |
|---|---|---|---|
| BRCA1 | OT1 | −1.41 | 2.66 |
| | OB1 | 0.38 | 0.77 |
| | OB3 | 0.44 | 0.74 |
| EGFR | OT1 | −4.00 | 15.96 |
| | OB1 | 0.08 | 0.94 |
| | OB3 | 0.01 | 0.99 |

TABLE 39 a, b, c and d-continued for BRCA1, EGFR, PTEN, BRAF:

| | | | |
|---|---|---|---|
| PTEN | OT1 | 3.18 | 0.11 |
| | OB1 | 1.03 | 0.49 |
| | OB3 | 0.79 | 0.58 |
| BRAF | OT1 | 2.61 | 0.16 |
| | OB1 | 1.13 | 0.46 |
| | OB3 | 1.55 | 0.34 |

From the above table it can be inferred that EGFR is being over expressed in the OT 1 sample. All the other genes seem to be normally expressing.

Figure 4:
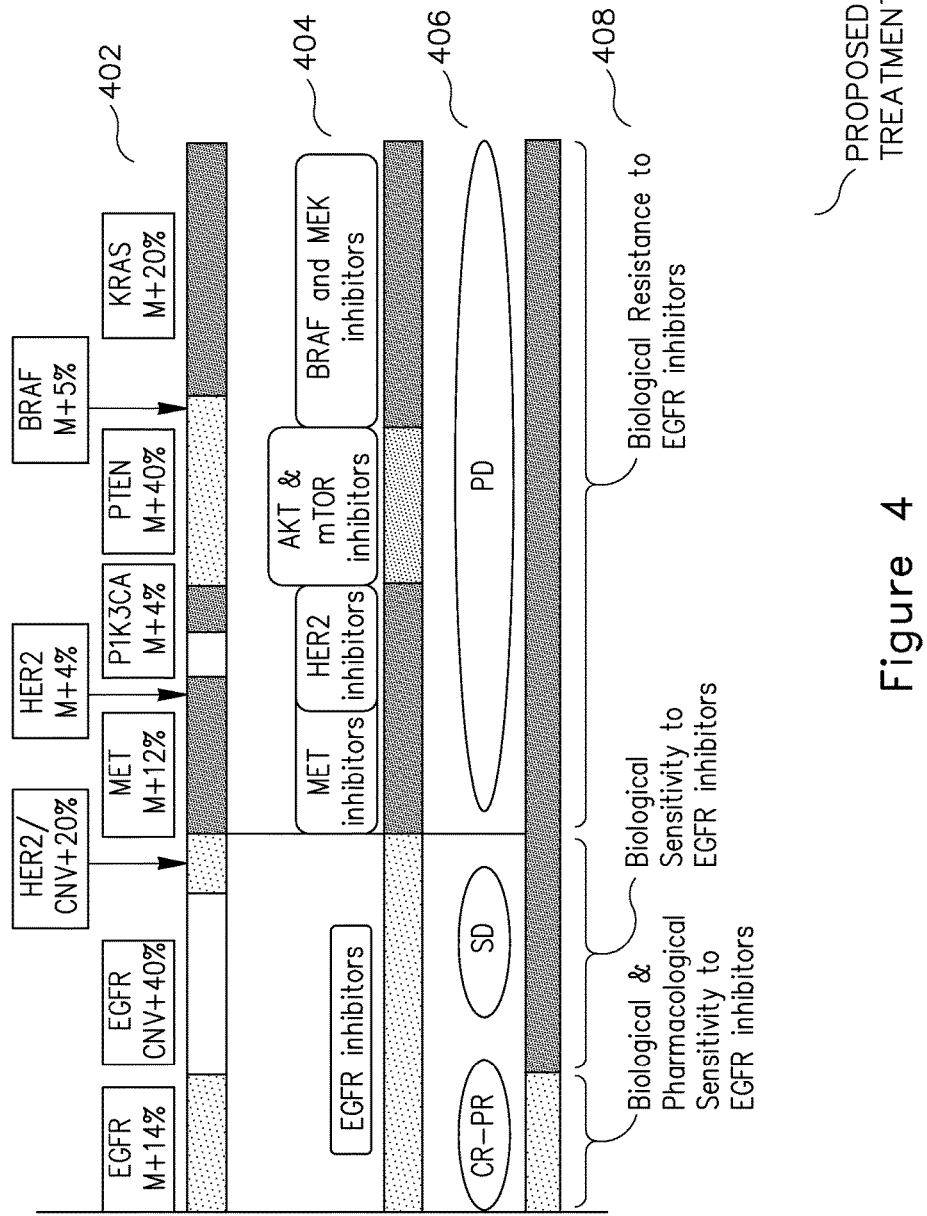
FIG. 4 shows proposed treatment 400 blocks for certain genes that are over expressed and the suitable inhibitors.

Personalized Treatment:

Gene expression value analysis provides various insights on up regulation or down regulation of multiple genes. In FIG. 4, the upper horizontal bar 402 represents genes affected by copy number variations (CNV) or Mutations and their frequency. The middle bar 404 indicates the target of potential signal transduction therapies associated with the particular molecular subtype. The lower bar indicates 406 as an example if clinical treatment is done by epidermal growth factor receptors (EGFR) targeted by tyrosine kinase (TK) inhibitors. Activation of downstream signaling molecules confers resistance to EGFR inhibitors, but may provide an ideal target for other therapies. AKT, protein kinase B; CR, complete response; HER2, human epidermal growth factor receptor-2; MEK, mitogen-activated protein kinase; mTOR, mammalian target of rapamycin; PD, progressive disease; PR, partial response; PIK3CA, phosphoinositide 3-kinase; PTEN, phosphatase and tensin homologue; SD, stable disease.

What is claimed is:

1. A method comprising:

isolating a sample from a subject suffering from a disease to measure gene expression values for a portfolio of genes;

measuring the gene expression values for the portfolio of genes based on determining an amount of RNA produced by each gene that can code for one of: a protein and a peptide;

analyzing, through a processor, the gene expression values for the portfolio of genes within said sample through repeatedly applying at least one of: penalized discriminant analyses and recursive feature elimination, said portfolio of genes being one of: a set of SEQ ID NO. 22 to SEQ ID NO. 43 and a combination of SEQ ID NOs thereof;

obtaining, through the processor, a gene expression value profile of the portfolio of genes for the sample from the subject based on the analysis of the gene expression values, the gene expression value profile comprising a statistically significant number of genes that vary in expression value from an expression value of the same genes in at least one of: a normal and a disease control sample; and normalizing, through the processor, a gene expression level of the portfolio of genes using a house keeping gene, the at least one of: the normal and the disease control sample and the sample from the subject in addition to obtaining the gene expression value profile, the house keeping gene being GAPDH.

2. The method of claim 1, further comprising:

performing a statistical analysis on the gene expression level for the portfolio of genes, a statistically significant value associated therewith representing collectively a level of gene expression values for the portfolio of genes that indicates that said subject has at least one of: a cancer, a progression of the cancer, an effect of treatment for the cancer and a location of the cancer.

3. The method of claim 1, wherein the disease is breast cancer.

4. The method of claim 1, wherein the sample is at least one of: a biopsy sample, a fine needle aspirate, parafilm embedded samples, a tumor tissue, immune cells, whole blood, saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a patient having cancer.

5. A method of diagnosing cancer, comprising:

analyzing, through a processor, gene expression values for a portfolio of genes within a sample from a subject through repeatedly applying at least one of: penalized discriminant analyses and recursive feature elimination, said portfolio of genes being one of: a set of SEQ ID NO. 22 to SEQ ID NO. 43 and a combination of SEQ ID NOs thereof;

obtaining, through the processor, a gene expression value profile of the portfolio of genes for the sample from the subject based on the analysis of the gene expression values, the gene expression value profile comprising a statistically significant number of genes that vary in expression value from an expression value of the same genes in at least one of: a normal and a control sample;

normalizing, through the processor, a gene expression level of the portfolio of genes using a house keeping gene, the at least one of: the normal and the control sample and the sample from the subject in addition to obtaining the gene expression value profile, the house keeping gene being GAPDH; and identifying differential modulation of each gene relative to the expression of the same genes in the at least one of: the normal and the control sample in the portfolio of genes in accordance with the analysis related to the obtained gene expression value profile and the normalized gene expression level, the differential modulation of the each gene indicating activation thereof to one of: a higher level and a lower level in the sample of the subject relative to expression thereof in the at least one of: the normal and the control sample.

6. The method of claim 5, wherein the cancer to be diagnosed is breast cancer.

7. The method of claim 5, wherein the sample from the subject is breast tissue, and the method further comprises:

creating a report summarizing data obtained by the analysis of the gene expression values.

* * * * *

SEQUENCE LISTING

```
<160> NUMBER OF SEQ ID NOS: 61

<210> SEQ ID NO 1
<211> LENGTH: 20
<212> TYPE: DNA
<213> ORGANISM: Homo sapiens

<400> SEQUENCE: 1
gcttctccct gacatccgtg                                              20

<210> SEQ ID NO 2
<211> LENGTH: 20
<212> TYPE: DNA
<213> ORGANISM: Homo sapiens

<400> SEQUENCE: 2
ggcccatggt accaggagtg                                              20

<210> SEQ ID NO 3
<211> LENGTH: 22
<212> TYPE: DNA
<213> ORGANISM: Homo sapiens

<400> SEQUENCE: 3
ggagctgcag atgctgacca ac                                           22

<210> SEQ ID NO 4
<211> LENGTH: 21
<212> TYPE: DNA
<213> ORGANISM: Homo sapiens

<400> SEQUENCE: 4
gtttctccag actgttgact g                                            21

<210> SEQ ID NO 5
<211> LENGTH: 21
<212> TYPE: DNA
<213> ORGANISM: Homo sapiens

<400> SEQUENCE: 5
cgcatgttcc gggacaaaag c                                            21

<210> SEQ ID NO 6
<211> LENGTH: 20
<212> TYPE: DNA
<213> ORGANISM: Homo sapiens
```

-continued

<400> SEQUENCE: 6
cgctctccct cgcagaactc					20

<210> SEQ ID NO 7
<211> LENGTH: 20
<212> TYPE: DNA
<213> ORGANISM: Homo sapiens

<400> SEQUENCE: 7
agaggtccaa ggtgccctac					20

<210> SEQ ID NO 8
<211> LENGTH: 20
<212> TYPE: DNA
<213> ORGANISM: Homo sapiens

<400> SEQUENCE: 8
cggacatcca ggcactgaag					20

<210> SEQ ID NO 9
<211> LENGTH: 23
<212> TYPE: DNA
<213> ORGANISM: Homo sapiens

<400> SEQUENCE: 9
gcaatttagg tatgaaagcc agc				23

<210> SEQ ID NO 10
<211> LENGTH: 23
<212> TYPE: DNA
<213> ORGANISM: Homo sapiens

<400> SEQUENCE: 10
ctttcagcat tttgacggca acc				23

<210> SEQ ID NO 11
<211> LENGTH: 18
<212> TYPE: DNA
<213> ORGANISM: Homo sapiens

<400> SEQUENCE: 11
ccgccaggaa cgtgcttg					18

<210> SEQ ID NO 12
<211> LENGTH: 18
<212> TYPE: DNA
<213> ORGANISM: Homo sapiens

<400> SEQUENCE: 12
gcagcctcac attgcccc					18

<210> SEQ ID NO 13
<211> LENGTH: 21
<212> TYPE: DNA
<213> ORGANISM: Homo sapiens

<400> SEQUENCE: 13
accgatggct tcgacgagtt c					21

<210> SEQ ID NO 14
<211> LENGTH: 20
<212> TYPE: DNA
<213> ORGANISM: Homo sapiens

<400> SEQUENCE: 14
agcccttgca gccctcacag                                          20

<210> SEQ ID NO 15
<211> LENGTH: 30
<212> TYPE: DNA
<213> ORGANISM: Homo sapiens

<400> SEQUENCE: 15
agcatttggt tttaaattat ggagtatatt                                30

<210> SEQ ID NO 16
<211> LENGTH: 30
<212> TYPE: DNA
<213> ORGANISM: Homo sapiens

<400> SEQUENCE: 16
atctatagtc atgctgaaag taggagaaag                                30

<210> SEQ ID NO 17
<211> LENGTH: 30
<212> TYPE: DNA
<213> ORGANISM: Homo sapiens

<400> SEQUENCE: 17
ctgaatagtc ctacagtgtt ttcagtttca                                30

<210> SEQ ID NO 18
<211> LENGTH: 20
<212> TYPE: DNA
<213> ORGANISM: Homo sapiens

<400> SEQUENCE: 18
ggcccacttc accgtactaa                                          20

<210> SEQ ID NO 19
<211> LENGTH: 20
<212> TYPE: DNA
<213> ORGANISM: Homo sapiens

<400> SEQUENCE: 19
gtggtttcaa ggccagatgt                                          20

<210> SEQ ID NO 20
<211> LENGTH: 20
<212> TYPE: DNA
<213> ORGANISM: Homo sapiens

<400> SEQUENCE: 20
caaggaaact ggccacaaat                                          20

<210> SEQ ID NO 21
<211> LENGTH: 20
<212> TYPE: DNA
<213> ORGANISM: Homo sapiens

<400> SEQUENCE: 21
ggggctttgt aaggagaacc                                          20

<210> SEQ ID NO 22
<211> LENGTH: 18
<212> TYPE: DNA

<213> ORGANISM: Homo sapiens

<400> SEQUENCE: 22
tgcttgaagt ctcccttg                                                    18

<210> SEQ ID NO 23
<211> LENGTH: 18
<212> TYPE: DNA
<213> ORGANISM: Homo sapiens

<400> SEQUENCE: 23
cttccattga agggtctg                                                    18

<210> SEQ ID NO 24
<211> LENGTH: 20
<212> TYPE: DNA
<213> ORGANISM: Homo sapiens

<400> SEQUENCE: 24
acccttgcag gtctaaatgg                                                  20

<210> SEQ ID NO 25
<211> LENGTH: 18
<212> TYPE: DNA
<213> ORGANISM: Homo sapiens

<400> SEQUENCE: 25
tgcctgcttt actgcaag                                                    18

<210> SEQ ID NO 26
<211> LENGTH: 19
<212> TYPE: DNA
<213> ORGANISM: Homo sapiens

<400> SEQUENCE: 26
gaagaccttc agaaggttg                                                   19

<210> SEQ ID NO 27
<211> LENGTH: 18
<212> TYPE: DNA
<213> ORGANISM: Homo sapiens

<400> SEQUENCE: 27
tggggagaat atgcagtg                                                    18

<210> SEQ ID NO 28
<211> LENGTH: 18
<212> TYPE: DNA
<213> ORGANISM: Homo sapiens

<400> SEQUENCE: 28
ggacttgtga gtactctg                                                    18

<210> SEQ ID NO 29
<211> LENGTH: 17
<212> TYPE: DNA
<213> ORGANISM: Homo sapiens

<400> SEQUENCE: 29
agtgggtgtt gaatgtg                                                     17

<210> SEQ ID NO 30
<211> LENGTH: 18

```
<212> TYPE: DNA
<213> ORGANISM: Homo sapiens

<400> SEQUENCE: 30
ggacaatcgc caattcag                                                  18

<210> SEQ ID NO 31
<211> LENGTH: 18
<212> TYPE: DNA
<213> ORGANISM: Homo sapiens

<400> SEQUENCE: 31
tggtggtgct ttgatctg                                                  18

<210> SEQ ID NO 32
<211> LENGTH: 18
<212> TYPE: DNA
<213> ORGANISM: Homo sapiens

<400> SEQUENCE: 32
ttagcaggaa aggcactg                                                  18

<210> SEQ ID NO 33
<211> LENGTH: 19
<212> TYPE: DNA
<213> ORGANISM: Homo sapiens

<400> SEQUENCE: 33
cagcttcatc ctacacaag                                                 19

<210> SEQ ID NO 34
<211> LENGTH: 20
<212> TYPE: DNA
<213> ORGANISM: Homo sapiens

<400> SEQUENCE: 34
gacagactga tgtgtatacg                                                20

<210> SEQ ID NO 35
<211> LENGTH: 20
<212> TYPE: DNA
<213> ORGANISM: Homo sapiens

<400> SEQUENCE: 35
gtgtaaatag ctggagatgg                                                20

<210> SEQ ID NO 36
<211> LENGTH: 20
<212> TYPE: DNA
<213> ORGANISM: Homo sapiens

<400> SEQUENCE: 36
atggtgatgt ggcagtgaaa                                                20

<210> SEQ ID NO 37
<211> LENGTH: 20
<212> TYPE: DNA
<213> ORGANISM: Homo sapiens

<400> SEQUENCE: 37
tagccagttg tggctttgtg                                                20

<210> SEQ ID NO 38
```

```
<210> SEQ ID NO 38
<211> LENGTH: 20
<212> TYPE: DNA
<213> ORGANISM: Homo sapiens

<400> SEQUENCE: 38
agggcagttt ggatagctca                                              20

<210> SEQ ID NO 39
<211> LENGTH: 20
<212> TYPE: DNA
<213> ORGANISM: Homo sapiens

<400> SEQUENCE: 39
caccacccca aaatctcaac                                              20

<210> SEQ ID NO 40
<211> LENGTH: 20
<212> TYPE: DNA
<213> ORGANISM: Homo sapiens

<400> SEQUENCE: 40
agtacctggg tctggacgtg                                              20

<210> SEQ ID NO 41
<211> LENGTH: 20
<212> TYPE: DNA
<213> ORGANISM: Homo sapiens

<400> SEQUENCE: 41
ctgggaactc aagcaggaag                                              20

<210> SEQ ID NO 42
<211> LENGTH: 19
<212> TYPE: DNA
<213> ORGANISM: Homo sapiens

<400> SEQUENCE: 42
cttgtgcagg attgttgtg                                               19

<210> SEQ ID NO 43
<211> LENGTH: 19
<212> TYPE: DNA
<213> ORGANISM: Homo sapiens

<400> SEQUENCE: 43
gccaattgta ggaacacag                                               19

<210> SEQ ID NO 44
<211> LENGTH: 20
<212> TYPE: DNA
<213> ORGANISM: Homo sapiens

<400> SEQUENCE: 44
ctgtcctggg cagaaagaag                                              20

<210> SEQ ID NO 45
<211> LENGTH: 20
<212> TYPE: DNA
<213> ORGANISM: Homo sapiens

<400> SEQUENCE: 45
ggtgagaggg aaggaacctc                                              20
```

```
<210> SEQ ID NO 46
<211> LENGTH: 20
<212> TYPE: DNA
<213> ORGANISM: Homo sapiens

<400> SEQUENCE: 46
gagagcgagc gagagagaaa                                               20

<210> SEQ ID NO 47
<211> LENGTH: 20
<212> TYPE: DNA
<213> ORGANISM: Homo sapiens

<400> SEQUENCE: 47
gctggagtcg gagtcttgtc                                               20

<210> SEQ ID NO 48
<211> LENGTH: 20
<212> TYPE: DNA
<213> ORGANISM: Homo sapiens

<400> SEQUENCE: 48
cagaagcgct gatggtcata                                               20

<210> SEQ ID NO 49
<211> LENGTH: 20
<212> TYPE: DNA
<213> ORGANISM: Homo sapiens

<400> SEQUENCE: 49
tcggcagttt tgggttattc                                               20

<210> SEQ ID NO 50
<211> LENGTH: 20
<212> TYPE: DNA
<213> ORGANISM: Homo sapiens

<400> SEQUENCE: 50
gcagaaaacg gagagtgctt                                               20

<210> SEQ ID NO 51
<211> LENGTH: 20
<212> TYPE: DNA
<213> ORGANISM: Homo sapiens

<400> SEQUENCE: 51
aaagcaagaa ggagcaggtg                                               20

<210> SEQ ID NO 52
<211> LENGTH: 20
<212> TYPE: DNA
<213> ORGANISM: Homo sapiens

<400> SEQUENCE: 52
ggccactgat tgtgccttat                                               20

<210> SEQ ID NO 53
<211> LENGTH: 20
<212> TYPE: DNA
<213> ORGANISM: Homo sapiens

<400> SEQUENCE: 53
tctttcttcc cttccccagt                                               20
```

```
<210> SEQ ID NO 54
<211> LENGTH: 20
<212> TYPE: DNA
<213> ORGANISM: Homo sapiens

<400> SEQUENCE: 54
attaaccctg ctcggtcctt                                               20

<210> SEQ ID NO 55
<211> LENGTH: 20
<212> TYPE: DNA
<213> ORGANISM: Homo sapiens

<400> SEQUENCE: 55
accctggagt tgatgtcgtc                                               20

<210> SEQ ID NO 56
<211> LENGTH: 20
<212> TYPE: DNA
<213> ORGANISM: Homo sapiens

<400> SEQUENCE: 56
ggcccacttc accgtactaa                                               20

<210> SEQ ID NO 57
<211> LENGTH: 20
<212> TYPE: DNA
<213> ORGANISM: Homo sapiens

<400> SEQUENCE: 57
gtggtttcaa ggccagatgt                                               20

<210> SEQ ID NO 58
<211> LENGTH: 20
<212> TYPE: DNA
<213> ORGANISM: Homo sapiens

<400> SEQUENCE: 58
caaggaaact ggccacaaat                                               20

<210> SEQ ID NO 59
<211> LENGTH: 20
<212> TYPE: DNA
<213> ORGANISM: Homo sapiens

<400> SEQUENCE: 59
ggggctttgt aaggagaacc                                               20

<210> SEQ ID NO 60
<211> LENGTH: 20
<212> TYPE: DNA
<213> ORGANISM: Homo sapiens

<400> SEQUENCE: 60
ctttgccttt gctggacttc                                               20

<210> SEQ ID NO 61
<211> LENGTH: 20
```

```
<212> TYPE: DNA
<213> ORGANISM: Homo sapiens

<400> SEQUENCE: 61
ccgtccttga tatggattgg                                              20
```